United States Patent [19]

Cole et al.

[11] Patent Number: 4,883,531
[45] Date of Patent: Nov. 28, 1989

[54] THREAD FRICTION MEASUREMENT ARRANGEMENT

[76] Inventors: Michael Cole, 6 Beedy Road, Scraptoft, Leicester; Dennis L. Munden, The Paddock, Ford View Close, Great Glen, Leicester; Marilynn J. Ryan, 32 Dominion Road, Glenfield, Leicester, LE3 8FA, all of England

[21] Appl. No.: 198,731

[22] Filed: May 25, 1988

[30] Foreign Application Priority Data

May 29, 1987 [GB] United Kingdom ................. 8712658

[51] Int. Cl.$^4$ .......................................... G01N 19/02
[52] U.S. Cl. .......................................... 73/9; 73/160; 73/862.39
[58] Field of Search ......................... 73/9, 160, 862.39

[56] References Cited

U.S. PATENT DOCUMENTS

| | | | |
|---|---|---|---|
| 2,285,255 | 6/1942 | Davis | 73/9 X |
| 2,378,614 | 6/1945 | Zahn | 73/160 X |
| 2,407,545 | 9/1946 | Fish | 73/160 X |
| 2,625,040 | 1/1953 | Ireland, Jr. | 73/9 X |
| 2,990,713 | 7/1961 | Heffelfinger et al. | 73/9 |
| 3,209,589 | 10/1965 | Schlatter | 73/160 |
| 3,324,719 | 6/1967 | Segrave | 73/160 |
| 3,831,444 | 8/1974 | Sasaki et al. | 73/9 X |
| 4,000,641 | 1/1977 | Lewis | 73/9 |
| 4,026,141 | 5/1977 | Merritt | 73/9 |

FOREIGN PATENT DOCUMENTS

| | | | |
|---|---|---|---|
| 1259602 | 1/1968 | Fed. Rep. of Germany | 73/9 |
| 228330 | 10/1986 | Japan | 73/9 |
| 284628 | 12/1986 | Japan | |
| 154701 | 10/1963 | U.S.S.R. | 73/160 |
| 723433 | 3/1980 | U.S.S.R. | 73/9 |
| 842919 | 7/1960 | United Kingdom | 73/9 |

OTHER PUBLICATIONS

"A Device for Studying the Frictional Properties of Fiber"; *The Australian Journal of Science*, Jun. 1945; pp. 173–174; E. H. Mercer.

"Method of Determining the Coefficient of Friction of Polymer Monofilaments"; *Polymer Mechanics*, vol. 7, No. 4, pp. 649–650, Dec. 1973; N. Yarsteva et al.

"Thread Friction of Synthetic Yarns"; *Melliand Textilberichte International*, vol. 56, No. 5, pp. 348–352; May 1975; Dr Thomas Longe (Ingerman with English Abstrct).

English Abstract of Japanese Patent Document 61-284628 (Ref. N); Patent Abstracts of Japan; vol. 11, No. 147, p. 575; Abstract published May 14, 1987 (from JPOABS).

*Primary Examiner*—Tom Noland
*Attorney, Agent, or Firm*—Charles J. Brown

[57] ABSTRACT

There is disclosed a thread friction measuring arrangement comprising first and second strain gauges arranged in a thread path either side of a cylindrical surface against which friction is to be measured so that the first and second strain gauges give electrical outputs respectively corresponding to the tension in the thread before and after turning around the surface, and further comprising electronic components for computing the frictional coefficient of the thread in the surface from the electrical outputs.

1 Claim, 1 Drawing Sheet

THREAD FRICTION MEASUREMENT ARRANGEMENT

This invention relates to thread friction measurement.

BACKGROUND TO THE INVENTION

Thread friction is conventionally measured by hauling a thread over a cylindrical surface and measuring the tension in the thread either side of the surface. If $T_1$ is the input tension, $T_2$ is the output tension and $\theta$ is the angle the thread turns around the cylindrical surface, the coefficient of friction $\mu$ is calculated from the relationship $$T_2/T_1 = e\mu^{\theta}$$

which gives $\mu = (\log T_2 - \log T_1)/\theta$

Conventional methods for measuring thread tension involve running the thread in a thread path including a roller displaceable against a resilient bias and measuring the displacement of the roller. Using such tension measuring arrangements for friction measurement results in a complicated arrangement and this complication is reflected in the cost of equipment commercially available for measuring thread frictional coefficients.

The present invention provides a simpler and therefore more reliable and less expensive thread friction measuring arrangement.

SUMMARY OF THE INVENTION

The invention comprises a thread friction measuring arrangement comprising first and second strain gauges arranged in a thread path to either side of a cylindrical surface against which friction is to be measured so that the said first and second strain gauges give electrical outputs respectively corresponding to the tension in the thread before and after turning around the said surface, and further comprising electronic means computing the frictional coefficient of the thread on the surface from the said electrical outputs.

Said thread path may be defined between input and output guides, and the thread may bend, in said thread path, substantially 180° around guides attached to each of said first and second strain gauges.

Said cylindrical surface may be replaceable, and the arrangement may comprise a set of interchangeable cylindrical surfaces of different materials against which frictional coefficients can be measured.

Said electronic means may comprise a microprocessor which preferably has a digital readout for the computed value of the frictional coefficient. The arrangement may include analogue-to-digital converter means between said strain gauges and said microprocessor—a single such converter may be used with multiplexing of signals from said first and second strain gauges.

The microprocessor may sample the signals from the analogue-to-digital converter means at intervals to compute the value of the instantaneous frictional coefficient.

The arrangement may also be used as a tension measuring arrangement by being adapted to display a thread tension computed from the output of at least one of said first and second strain gauges. For this purpose, said cylindrical surface may be replaceable by a low friction roller.

The arrangement may be comprised in a portable casing, which may also comprise a thread hauling arrangement which may comprise a driven winding drum.

BRIEF DESCRIPTION OF THE DRAWINGS

One embodiment of a thread friction measuring arrangement according to the invention will now be described with reference to the accompanying drawings, in which.

DETAILED DISCLOSURE OF THE PREFERRED EMBODIMENT

Figure 1:
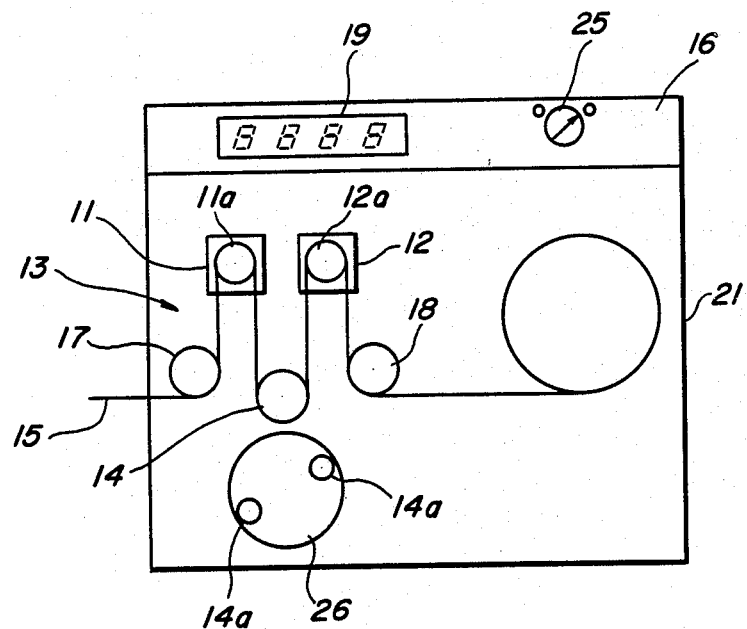
FIG. 1 is an elevation of the arrangement.
Figure 2:
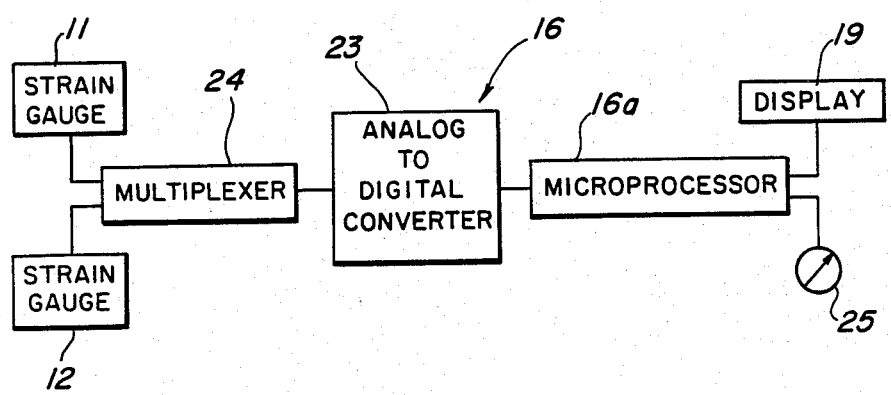
FIG. 2 is a block diagram of the electronic arrangement.

FIGS. 1 and 2 illustrate a thread friction measuring arrangement comprising first and second strain gauges 11, 12 arranged in a thread path 13 to either side of a cylindrical surface 14 against which friction is to be measured so that the gauges 11, 12 give electrical outputs respectively corresponding to the tension in the thread 15 before and after turning around the said surface 14, and further comprising electronic means 16 computing the frictional coefficient of the thread 15 on the surface 14 from the said electrical outputs.

The thread path 13 is defined between input and output guides 17, 18 and the thread 15 bends, in said thread path 13, about 180° around guides 11a, 12a attached to the strain gauges 11, 12. The guides 11a, 12a are low friction rollers so that the tension in the thread 15 either side of the guide 11a is substantially equal, and the same is true of the thread tension either side of the guide 12a, though this tension will of course in general be different from the tension around the guide 11a.

The said cylindrical surface 14 is replaceable, the arrangement comprising a set of interchangeable cylinders having surfaces for example of chromium, ceramic, synthetic sapphire and other materials against which it may be desired to measure the frictional coefficients of threads.

The said electronic means comprise a microprocessor 16a connected to a digital readout 19. In addition to computing the frictional coefficient, of course, the microprocessor can be programmed also to display the tension in the thread 15 as measured by the one or the other strain gauge 11, 12. The cylindrical surface 14 may, however, for the measurement of tension, be replaced by a low friction roller so that passage of the thread through the arrangement does not significantly affect thread tension and the tension is sensibly constant between the input and output guides 17, 18 (which may also comprise low friction rollers) and the outputs of the strain gauges 11, 12 may be averaged.

The arrangement may be comprised in a portable casing 21 which also houses a thread hauling arrangement comprising, as illustrated, a motor driven winding drum 22.

FIG. 2 illustrates in block diagram form the electronic arrangement 16 comprising the microprocessor 16a which is fed with digital signals, corresponding to the analogue voltage outputs of the strain gauges, from analogue-to-digital converter means 23, which may comprise separate channels for each strain gauge 11, 12 or which may, as illustrated, comprise a single channel arrangement with a multiplexer 24 for the strain gauges.

The multiplexer 24 is controlled by the microprocessor 16a, which has a mode switch 25 to select whether the computed frictional coefficient or the measured thread tension is output to the display 19.

The arrangement can be used in a dynamic capacity as a tension controller. Illustrated in FIG. 1 are further cylindrical friction surfaces 14a mounted on a rotatable head 26 adjacent the first such cylindrical surface 14. By suitably arranging the thread path over the cylindrical surfaces 14, 14a, the total angle 0 the yarn bends around the surfaces can be varied by rotation of the head 26. This rotation can be controlled by a force transducer or a motor controlled by the microprocessor 16a so as to maintain the output tension constant at a preselected level or, if desired, even to introduce a desired pattern or sequence of tension variations into the same while compensating for frictional coefficient irregularities.

We claim:

1. A thread friction measuring arrangement comprising first and second strain gauges arranged in a thread path to either side of a cylindrical surface against which friction is to be measured so that the said first and second strain gauges give first and second electrical outputs respectively corresponding to the tension in the thread before and the second tension in the thread after turning around the said surface so as to turn through an angle 0, and further comprising electronic means computing the frictional coefficient of the thread on the surface from the said electrical outputs, said electronic means comprising logarithm evaluating means evaluating logarithms of said first and second outputs, and computing means subtracting the logarithm of said first output from the logarithm of said second output, and output means outputting the result of such subtraction divided by the angle $\theta$.

* * * * *

UNITED STATES PATENT AND TRADEMARK OFFICE
CERTIFICATE OF CORRECTION

PATENT NO. : 4,883,531
DATED : November 28, 1989
INVENTOR(S) : Michael Cole, Dennis L. Munden, Marilynn J. Ryan It is certified that error appears in the above-identified patent and that said Letters Patent is hereby corrected as shown below:

On the title page, lefthand column, after identification of the Inventors in entry [75] and before identification of the Application Serial No. [21] insert:

--[73] Assignee: Leicester Polytechnic, Leicester, England--

Signed and Sealed this

Fifth Day of March, 1991

*Attest:*

HARRY F. MANBECK, JR.

*Attesting Officer*     *Commissioner of Patents and Trademarks*